United States Patent [19]

McFarlane

[11] Patent Number: 4,573,981
[45] Date of Patent: * Mar. 4, 1986

[54] PROTECTIVE SHEATH STRUCTURE FOR A CATHETER ASSEMBLY

[76] Inventor: Richard H. McFarlane, 2571 Kaneville Rd., Geneva, Ill. 60134

[*] Notice: The portion of the term of this patent subsequent to Feb. 19, 2002 has been disclaimed.

[21] Appl. No.: 544,464

[22] Filed: Oct. 24, 1983

[51] Int. Cl.$^4$ ............................................. A61M 5/00
[52] U.S. Cl. ................................... 604/263; 604/192
[58] Field of Search .............. 604/263, 192, 193, 197, 604/198, 199, 280, 162, 163, 165, 240, 242

[56] References Cited

U.S. PATENT DOCUMENTS

| | | | |
|---|---|---|---|
| 3,225,763 | 12/1965 | Waterman | 604/192 |
| 3,677,247 | 7/1972 | Brown | 604/197 |
| 4,139,010 | 2/1979 | Dykstra | 604/263 |
| 4,334,536 | 6/1982 | Pfleger | 604/263 X |
| 4,362,156 | 12/1982 | Feller, Jr. et al. | 604/177 |
| 4,468,223 | 8/1984 | Minagawa | 604/263 X |
| 4,500,312 | 2/1985 | McFarlane | 604/263 |

*Primary Examiner*—Stephen C. Pellegrino
*Attorney, Agent, or Firm*—John C. Malloy

[57] ABSTRACT

A protective sheath structure of the type primarily designed to be selectively positioned and removed from a surrounding, protective and substantially enclosing position relative to the cannula portion of a catheter assembly. Selective engagement and disengagement of the sheath structure is accomplished through activation of a locking structure including a pair of oppositely disposed finger elements pivotally disposed to selectively engage and disengage correspondingly positioned flange structure on the base of the catheter assembly. Positioning ribs on the interior of the sheath body provides substantial centering of the cannula within the interior of the sheath.

11 Claims, 6 Drawing Figures

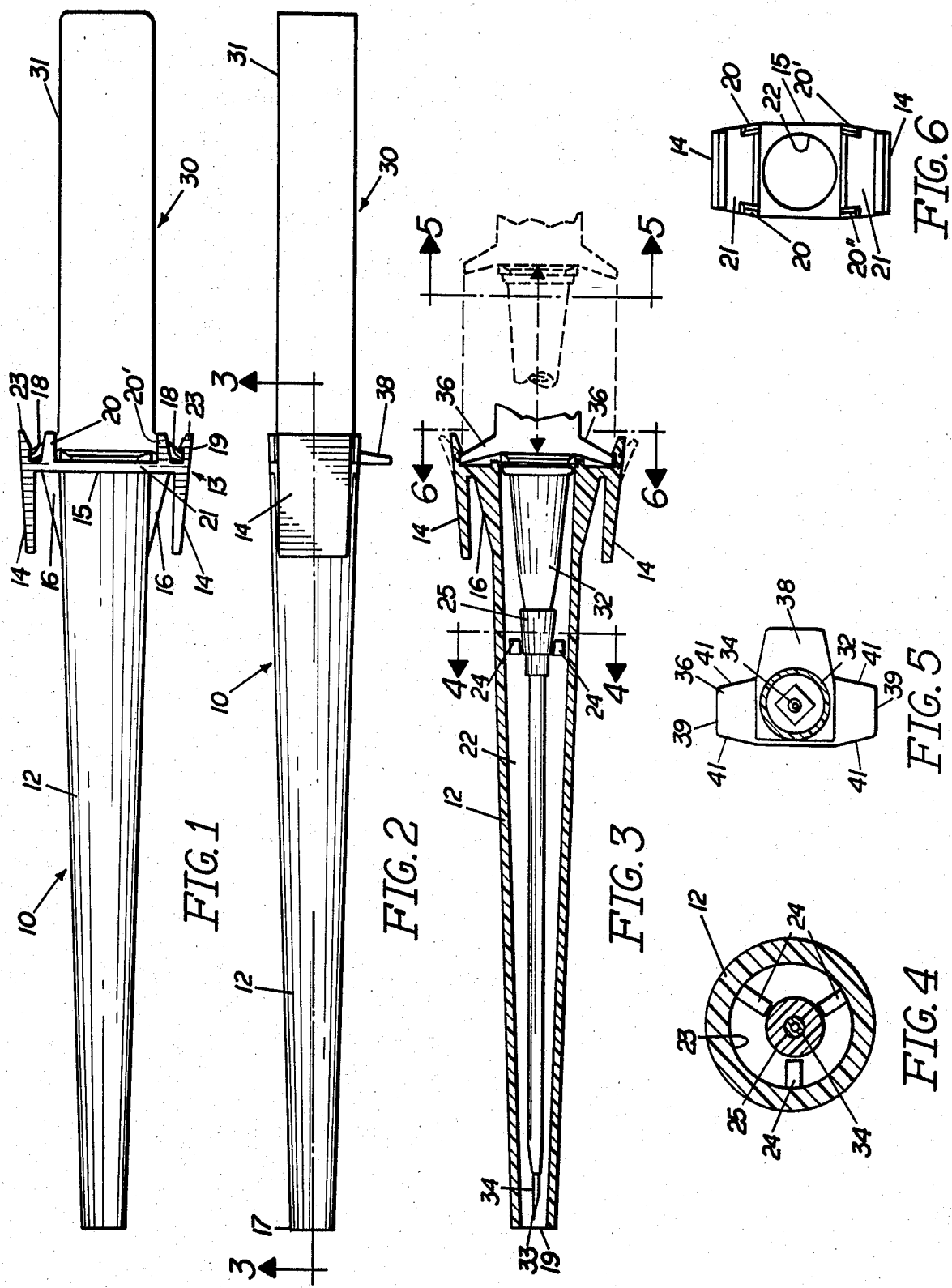

PROTECTIVE SHEATH STRUCTURE FOR A CATHETER ASSEMBLY

BACKGROUND OF THE INVENTION

1. Field of the Invention

This invention relates to a protective sheath structure used in combination with a catheter assembly to be removably mounted over the cannula portion of the catheter assembly thereby preventing inadvertent damage to the catheter trocar assembly or injury from puncturing the trocar portion of the assembly.

1. Description of the Prior Art

In the medical profession, catheters are commonly used with great frequency and because of such frequent and popular usage, numerous catheter designs including sheath or cover elements for the catheter structure have been designed. Common to all such protective covers is the requirement to adequately encase or surround the cannula and trocar portions of the catheter. This is done not only for security reasons but to maintain proper sterility of the structure by keeping it out of contact with unintended objects.

However, when it becomes necessary to use the catheter device on a patient, it is highly desirable in actual application for a sheath or cover structure to be readily removed from its protective position relative to the cannula. Such easy removal should be accomplished without unnecessary manipulation by the medical personnel involved.

While the prior art devices now in existence often accomplish the proper encasement or covering of the cannula, such sheaths or covering portions are frequently difficult to remove during the act of applying the catheter to the patient as intended. Further, structures specifically designed to accomplish ready removal of the sheath or protective structure often become disengaged inadvertently without the knowledge or intent of the medical personnel in charge. This results of course in a safety hazard or a ruining of the catheter inadvertently.

Therefore, it is obvious that there is a need in the medical industry for a catheter structure having a cover or sheath structure adequately designed to securely engage the catheter in its covered or protected position. Such a connecting assembly should be capable of securely locking the catheter in place while at the same time having structural facilities for easy removal of the sheath from the remainder of the catheter through disengagement of a locking portion thereof in a selected fashion. Finally, the overall structural configuration and material as well as the design and dimensions of the intended catheter and protective sheath should be such as to allow the entire assembly to be disposable thereby allowing its production at a relatively low price.

SUMMARY OF THE INVENTION

The present invention is directed towards a sheath structure of the type used for protection of the cannular and trocar portions of a catheter assembly. More specifically, the sheath structure includes a body means having a substantially elongated and preferably tapered configuration of sufficient length to completely enclose and extend beyond the enclosed cannula portion of the catheter assembly.

Locking means is integrally formed on the body of the sheath structure and includes two finger elements disposed on opposite sides of the body of the sheath. Each of the finger elements is spaced away from the body and extends substantially parallel to one another and the the longitudinal axis of the sheath. Each of the finger elements is effectively pivotally or movably connected to the body and thereby selectively positioned into and out of engaging, gripping or substantially locking relation to flange structure located on the base of the catheter assembly. More specifically, the flange structure includes two flange elements extending outwardly from opposite sides of the base of the catheter assembly. These flange elements are correspondingly located relative to the finger elements such that when the cannula portion of the catheter assembly is located in protected position within the interior of the sheath body, the flange elements are disposed in engageable, gripping relation to the finger elements.

Each finger element further includes a groove and a contiguously located lip portion wherein pivotal movement of the finger elements causes positioning of the lip portion of each finger element beyond and into substantially overlapping relation to a distal peripheral edge of each of flange element. Removal of the catheter assembly from the sheath structure is accomplished by pivotal movement of each of the finger elements wherein the lip portion again passes over the extreme distal edge of each of the flange elements and out of its grasping position relative to each of the flange elements.

Positioning means is disposed on the interior surface of the sheath body and preferably comprises a plurality of elongated ribs disposed in substantially equally spaced apart relation to one another so as to engage the outer or exterior surface of the cannula portion of the catheter assembly. A predetermined disposition of the rib element causes effective centering of the enclosed portion of the catheter assembly within the interior of the sheath body.

BRIEF DESCRIPTION OF THE DRAWINGS

For a fuller understanding of the nature of the present invention, reference will be had to the following detailed drawing, in which:

FIG. 1 is a top plan view of the protective sheath and accompanying catheter assembly of the present invention.

FIG. 2 is a side view of the embodiment of FIG. 1.

FIG. 3 is a sectional view along line 3—3 of FIG. 2 showing structural details and the relationship of the enclosed cannula portion of the catheter assembly to the sheath structure of the present invention.

FIG. 4 is a sectional view along line 4—4 of FIG. 3.

FIG. 5 is a sectional view along line 5—5 of FIG. 3.

FIG. 6 is an end view along line 6—6 of FIG. 3.

Similar reference characters refer to similar parts throughout the several views of the drawing.

DETAILED DESCRIPTION OF THE PREFERRED EMBODIMENTS

The present invention is directed to a shield structure generally indicated as 10 of the type designed to enclose the cannula and trocar portion of the catheter assembly wherein the catheter assembly is generally indicated as 30. The shield structure comprises a body 12 having a substantially elongated configuration and being somewhat tapered from the sheath base 15 to the distal end 17. Further, the body 12 has a hollow interior portion along the length thereof 22 and the body 12 as well as the interior portion 22 is specifically dimensioned and configured to entirely enclose the cannula portion 32 as well as the pointed tip 33 of the trocar portion 34. Other structural features of the body 12 comprises the distal end 17 defined by an apertured tip 19. However, the length of the body 12 is longer than that of the combined trocar 34 and cannula 32 such that the pointed tip 33 does not protrude through the aperture 19. With reference to FIGS. 3 and 6, the body 12 includes a base 15 disposed in contiguous and surrounding relation to an entrance aperture 22. This entrance 22 is sufficiently dimensioned to allow passage therethrough of the entire catheter assembly until the entire trocar and cannula are completely enclosed within the interior 22 of the body 12.

Further structural features of the shield structure 12 include a positioning means disposed on the interior 22 of the body 12. As best seen in FIGS. 3 and 4 the positioning means comprises a plurality of ribs 24 disposed in spaced apart relation to one another and extending outwardly from the interior surface 23 of the body 12. Preferably, each of the ribs extends outwardly towards the center or longitudinal axis of the body a sufficient distance to engage the base portion 25 of the cannula 32 as shown in both FIGS. 3 and 4. In that the base 25 is so engaged and effectively centered between the plurality of ribs 24, the cannula is effectively centered within the interior 22 and along the entire length of the body 12. This centering position avoids damage of the trocar 34 as the trocar and cannula enter the interior 22 as well as avoids damage during storage and/or shipment, when the cannula and trocar are maintained on the interior of the body 12.

Additional structural features of the present invention include locking means comprising a pair of locking fingers generally indicated as 13 and including a lever portion 14 and a gripping portion 19 integrally attached to one another. Each finger 13 is integrally connected to the base 15 of the body 12 of the sheath structure through the provision of connecting links 21. Further, the gripping portion 19 includes a lip 23 contiguously disposed to a groove 18 formed on the undersurface of the gripping portion 19 of each finger 13. In operation, the lever portion 14 of each finger is depressed towards the body 12. This allows pivotal movement of the finger about the connecting link 21 and a raising of the lip portion 23 so as to expose groove members 18. The base 31 of the catheter assembly includes flange structure comprising outwardly extending flange elements 36. These flange elements are angled forwardly such that their outermost edge is fit within the correspondingly positioned groove 18 of each finger 13. This is accomplished when the catheter is inserted within the sheath such that the cannula 32 and the trocar 34 are completely encased or covered. Release of the lever portion 14 of each finger causes the grooves to entirely enclose about the distal-most edges 39 of the flange structure 36 thereby effectively locking or securing the flange structure in connecting relation to the finger elements 13 a the lip portions 23 overlap each of the flange structures 36. Removal of the catheter assembly from the sheath may be accomplished again by depression of the lever portions 14 of each finger elements towards the body so as to again overexpose the grooves 18 and allow freeing or passage of the flange structures or flange elements 36 out of the grip of the locking fingers 13. The action and relative disposition and positioning of the flange elements 36 relative to the locking fingers 13 is best shown in FIG. 3. For clarity, a sectional view along line 5—5 shows structural features of the catheter assembly, at least some of which are not per se an integral part of the present invention. Namely, flange portion 38 is also secured to the base and is positioned to effectively remove the cannula from the trocar once the assembly is within a blood vessel of the patient. Forward movement of flange 28 by the thumb or other finger forces the cannula 32 forward off the end of the trocar at and past the tip 33 thereof.

Further structural features of the present invention include the provision of guide means including two pair of outwardly extending fingers 20 and 20'. The two fingers of each pair are disposed in spaced apart relation to one another a sufficient distance to engage or alternately overlap the lateral edges 41 of each flange structure once the cannula and trocar are completely enclosed on the interior 22 of the body 12. These guide fingers serve to properly orient the flange elements and accordingly the entire base 31 for communicating and engaging relation relative to the locking fingers 13.

What is claimed is:

1. A sheath structure of the type positioned in substantially enclosing, protective relation to a catheter assembly comprising:
   (a) said sheath structure including a body means having a substantially elongated configuration of a predetermined length sufficient to extend beyond the catheter assembly portion being enclosed,
   (b) entrance means including an opening formed at one end of the body means and dimensioned to allow passage of the enclosed catheter assembly portion therethrough,
   (c) locking means integrally formed on said body means adjacent said entrance means and structured to selectively engage and disengage a flange structure formed on the catheter assembly,
   (d) said locking means comprising two finger elements each pivotally connected on opposite sides of the body means and including a lever portion spaced from said body means and extending in substantially parallel relation to the other of said finger elements and away from said entrance means,
   (e) each finger element further including a gripping portion integrally secured to said lever portion and extending colinear therewith in the opposite direction, said gripping portion structured to lockingly engage the flange structure of the catheter assembly,
   (f) said flange structure comprising two flange elements extending outwardly from opposite sides of a catheter base of said catheter assembly, each flange element configured for grasping engagement by one of said finger elements,
   (g) guide means disposed adjacent said locking means and structured to orient said flange elements into communicating relation with said locking means,
   (h) whereby said sheath structure may be selectively secured to and removed from enclosing relation to said catheter assembly.

2. A sheath structure as in claim 1 wherein said body means comprises a substantially hollow interior extending along the length thereof, positioning means disposed on an interior surface of said body means and structured to engage the interior of the enclosed catheter assembly and thereby substantially center the catheter assembly within said hollow interior of said body means.

3. A sheath structure as in claim 2 wherein said positioning means comprises a plurality of ribs disposed in spaced apart relation to one another and extending outwardly from an interior surface of said body means toward the center longitudinal axis of said body means.

4. A sheath structure as in claim 1 wherein said gripping portion of each finger element comprises a groove extending transversely to the length of said finger element and substantially facing said opening, a lip element contiguous said groove and disposed in substantially overlapping relation to an edge of the flange structure gripped by the finger element.

5. A sheath structure as in claim 4 further comprising a sheath base integrally formed on said body means in surrounding relation to said opening of said entrance means, said sheath base including a connecting link disposed in interconnecting relation between said body means and each of said finger elements.

6. A sheath structure as in claim 5 wherein each of said finger elements is attached to said connecting link in substantially perpendicular relation thereto and spaced from said body means, each of said groove means integrally formed at the junction of one of said connecting links and said attached finger element.

7. A sheath structure as in claim 5 wherein said guide means extends outwardly from said sheath base in the same direction as said gripping portion and in spaced apart relation thereto, said guide means structured for engagement with opposite edges of the flange structure of said catheter assembly.

8. A sheath structure as in claim 7 wherein said guide means comprises two pairs of projections, each pair configured to border oppositely disposed peripheral edges of the flange structure of the catheter assembly, whereby the flange structure is maintained in place upon engagement of said finger element with the distal end of the flange structure.

9. A sheath structure as in claim 1 wherein said guide means comprises two pairs of projections, each pair configured to border oppositely disposed peripheral edges of each flange element, whereby each flange element is maintained in place upon engagement of said finger element with said distal end of each flange element.

10. A sheath structure as in claim 1 wherein said groove means is integrally formed on an undersurface of each of said finger elements an configured for mating engagement with a distal end of one said flange elements when said catheter assembly is positioned within said body means, whereby the catheter assembly is secured therein and fixedly attached to the body means.

11. A sheath structure as in claim 1 wherein said body means includes a substantially elongated continously convergent configuration extending from said entrance means to a distal end of said body means, said distal end of said body means defined by an apertured tip portion.

* * * * *